(12) United States Patent
Yeo

(10) Patent No.: US 8,823,940 B2
(45) Date of Patent: Sep. 2, 2014

(54) LIGHT ABSORBANCE MEASUREMENT METHOD AND APPARATUS

(71) Applicant: Samsung Electronics Co., Ltd., Suwon-si (KR)

(72) Inventor: Yeong Bae Yeo, Seoul (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 16 days.

(21) Appl. No.: 13/925,304

(22) Filed: Jun. 24, 2013

(65) Prior Publication Data

US 2013/0280818 A1 Oct. 24, 2013

Related U.S. Application Data

(63) Continuation of application No. 13/011,168, filed on Jan. 21, 2011.

(30) Foreign Application Priority Data

Feb. 5, 2010 (KR) .................. 10-2010-0011083

(51) Int. Cl.
*G01N 21/00* (2006.01)
*G01N 21/75* (2006.01)
(52) U.S. Cl.
USPC ............ 356/435; 356/433; 356/440; 436/164
(58) Field of Classification Search
USPC ................................................. 356/432–444
See application file for complete search history.

(56) References Cited

U.S. PATENT DOCUMENTS

| | | | | |
|---|---|---|---|---|
| 4,123,173 A * | 10/1978 | Bullock et al. | ................ | 356/246 |
| 4,234,539 A * | 11/1980 | Ginsberg et al. | ................ | 422/64 |
| 4,536,091 A * | 8/1985 | Allington | ....................... | 356/435 |
| 5,317,156 A * | 5/1994 | Cooper et al. | ................ | 250/345 |
| 6,721,053 B1 * | 4/2004 | Maseeh | ......................... | 356/436 |
| 7,170,609 B2 * | 1/2007 | Potyrailo et al. | .............. | 356/440 |
| 7,255,835 B2 * | 8/2007 | Franzen et al. | ............ | 422/82.11 |
| 7,604,776 B2 * | 10/2009 | Yamamoto et al. | ........... | 422/547 |
| 7,692,794 B2 * | 4/2010 | Kim et al. | ..................... | 356/418 |
| 8,542,362 B2 * | 9/2013 | Yeo | ................................ | 356/435 |
| 2009/0021741 A1 * | 1/2009 | Kim et al. | ..................... | 356/440 |
| 2009/0238724 A1 * | 9/2009 | Yamamoto et al. | .......... | 422/68.1 |
| 2011/0124132 A1 * | 5/2011 | Kim et al. | ..................... | 436/525 |

* cited by examiner

*Primary Examiner* — Gregory J Toatley
*Assistant Examiner* — Jarreas C Underwood
(74) *Attorney, Agent, or Firm* — Sughrue Mion, PLLC

(57) ABSTRACT

Methods and apparatuses for measuring a light absorbance are provided. The method measures light absorbance of at least one detection chamber of a microfluidic device, including the detection chamber and at least one reference chamber. The detection chamber may accommodate a test subject. The method includes detecting a plurality of reference transmitted light intensities for the at least one reference chamber and estimating a value between the plurality of reference transmitted light intensities through nonlinear approximation. The estimated value is then applied to light absorbance measurement of the detection chamber to reduce a light absorbance error of the detection chamber.

18 Claims, 10 Drawing Sheets

LIGHT ABSORBANCE MEASUREMENT METHOD AND APPARATUS

CROSS-REFERENCE TO RELATED APPLICATION

This application is a continuation application of U.S. application Ser. No. 13/011,168, filed Jan. 21, 2011, which claims priority from Korean Patent Application No. 10-2010-0011083, filed on Feb. 5, 2010 in the Korean Intellectual Property Office, the disclosures of which are incorporated herein by reference.

BACKGROUND

1. Field

Apparatuses and methods consistent with exemplary embodiments relate to measuring light absorbance of a test subject accommodated in a detection chamber of a microfluidic device.

2. Description of the Related Art

A variety of methods to analyze and test samples have been developed in various application fields such as environmental monitoring, food inspection, and medical diagnostics. However, related art test methods require numerous manual tasks and a variety of equipment. To test samples based on a prescribed protocol, a skilled tester must manually perform various processes such as reagent injection, mixture, separation and movement, reaction, and centrifugal separation a number of times. This manual test method may cause errors in test results.

A skilled clinical pathologist is needed to quickly perform such tests. In addition, even a skilled clinical pathologist may experience many difficulties in simultaneously performing various tests. There is a need to provide an apparatus capable of simultaneously, quickly, and accurately performing various pathological tests required under various circumstances, as obtaining rapid pathological test results is the most important factor in taking quick emergency measures for emergency patients.

An example of an apparatus capable of simultaneously, quickly, and accurately performing various pathological tests is a disc-shaped microfluidic device. Blood is injected into the disc-shaped microfluidic device and the microfluidic device is then rotated to create centrifugal force which separates a serum from the injected blood. The separated serum is mixed with a certain quantity of diluent and the mixture is moved to a number of reaction chambers in the microfluidic device. Different reagents corresponding respectively to various blood test items have already been injected into individual reaction chambers. Each of the different reagents in their respective reaction chambers reacts with the serum to exhibit a specific color. Blood analysis is carried out by detecting light absorbance based on changes in the exhibited color.

SUMMARY

One or more exemplary embodiments provide a light absorbance measurement method and apparatus that reduces a light absorbance measurement error caused by variation in an intensity of emission of a light source used for light absorbance detection.

One or more exemplary embodiments also provide a light absorbance measurement method and apparatus that enables quick light absorbance detection.

In accordance with an aspect of an exemplary embodiment, there is provided a method to measure light absorbance of at least one detection chamber of a microfluidic device including the detection chamber and at least one reference chamber, the detection chamber accommodating a test subject, the method including detecting a plurality of reference transmitted light intensities for the at least one reference chamber, and estimating a value between the plurality of reference transmitted light intensities through nonlinear approximation and applying the estimated value to light absorbance measurement of the detection chamber to reduce a light absorbance measurement error of the detection chamber.

A plurality of light sources to emit light of different wavelengths and a plurality of optical detectors corresponding to the plurality of light sources may be provided at positions corresponding to positions of the at least one reference chamber and the at least one detection chamber, and one of the plurality of light sources may be turned on and the other light sources may be turned off when transmitted light intensity detection is performed.

The at least one reference chamber may include a first reference chamber and a second reference chamber, and the plurality of reference transmitted light intensities may be detected in an order such that a reference transmitted light intensity of the first reference chamber is detected, a reference transmitted light intensity of the second reference chamber is detected, a reference transmitted light intensity of the first reference chamber is again detected.

The plurality of reference transmitted light intensities may be detected during one rotation period of the microfluidic device after one of the plurality of light sources is turned on.

The plurality of reference transmitted light intensities may be detected during a first rotation period of the microfluidic device after one of the plurality of light sources is turned on.

The plurality of reference transmitted light intensities may be detected during one rotation period of the microfluidic device other than a first rotation period, after one of the plurality of light sources is turned on.

A transmitted light intensity of the at least one detection chamber may be detected during the same rotation period as the rotation period of the microfluidic device during which the plurality of reference transmitted light intensities is detected after one of the plurality of light sources is turned on.

The at least one reference chamber may include a first reference chamber, a second reference chamber, and a third reference chamber, and the plurality of reference transmitted light intensities may be detected in an order such that a reference transmitted light intensity of the first reference chamber is detected, a reference transmitted light intensity of the second reference chamber is detected, a reference transmitted light intensity of the third reference chamber is detected, a reference transmitted light intensity of the first reference chamber is again detected, and a value between the detected reference transmitted light intensities may be estimated through nonlinear approximation.

The plurality of reference transmitted light intensities may be detected during one rotation period of the microfluidic device.

The plurality of reference transmitted light intensities may be detected during a first rotation period of the microfluidic device after one of the plurality of light sources is turned on.

The plurality of reference transmitted light intensities may be detected during one rotation period of the microfluidic device, other than a first rotation period, after one of the plurality of light sources is turned on.

A transmitted light intensity of the at least one detection chamber may be detected during the same rotation period as the rotation period of the microfluidic device during which the plurality of reference transmitted light intensities is detected after one of the plurality of light sources is turned on.

The at least one reference chamber may include only a single reference chamber, and the plurality of reference transmitted light intensities may be detected for the reference chamber and a value between the detected reference transmitted light intensities may be estimated through nonlinear approximation.

The plurality of reference transmitted light intensities may be detected during a plurality of rotation periods of the microfluidic device.

The plurality of reference transmitted light intensities may be detected during a plurality of consecutive rotation periods of the microfluidic device including a first rotation period of the microfluidic device after one of the plurality of light sources is turned on.

The plurality of reference transmitted light intensities may be detected during a plurality of consecutive rotation periods of the microfluidic device, other than a first rotation period, after one of the plurality of light sources is turned on.

A transmitted light intensity of the detection chamber may be detected during the same rotation periods as the plurality of rotation periods of the microfluidic device during which the plurality of reference transmitted light intensities is detected after one of the plurality of light sources is turned on.

In accordance with an aspect of another exemplary embodiment, there is provided a light absorbance measurement apparatus including a microfluidic device including at least one detection chamber and at least one reference chamber, the detection chamber accommodating a test subject, at least one light source to emit light to the at least one reference chamber and the detection chamber, at least one optical detector corresponding to the at least one light source, the optical detector detecting an intensity of light transmitted through the at least one reference chamber and the detection chamber, and a controller to detect a plurality of reference transmitted light intensities for the at least one reference chamber and to estimate a value between the plurality of reference transmitted light intensities through nonlinear approximation and to apply the estimated value to light absorbance measurement of the detection chamber.

The controller may calculate the light absorbance as a ratio between a reference transmitted light intensity of the reference chamber and a transmitted light intensity of the detection chamber.

The at least one light source may include a plurality of light sources and the at least one optical detector may include a plurality of optical detectors, the plurality of light sources and the plurality of optical detectors being provided at positions corresponding to positions of the at least one reference chamber and the detection chamber, and the controller may perform a control operation to turn on one of the plurality of light sources and to turn off the other light sources when transmitted light intensity detection is performed.

The at least one reference chamber may include a first reference chamber and a second reference chamber, and the controller may detect the plurality of reference transmitted light intensities in an order such that a reference transmitted light intensity of the first reference chamber is detected, a reference transmitted light intensity of the second reference chamber is detected, a reference transmitted light intensity of the first reference chamber is again detected, and may estimate a value between the detected reference transmitted light intensities through nonlinear approximation.

The first reference chamber, the second reference chamber, and the detection chamber may be provided in a concentric arrangement on the microfluidic device.

The at least one reference chamber may include a first reference chamber, a second reference chamber, and a third reference chamber, and the controller may detect the plurality of reference transmitted light intensities in an order such that a reference transmitted light intensity of the first reference chamber is detected, a reference transmitted light intensity of the second reference chamber is detected, a reference transmitted light intensity of the third reference chamber is detected, a reference transmitted light intensity of the first reference chamber is again detected, and may estimate a value between the detected reference transmitted light intensities through nonlinear approximation.

The first reference chamber, the second reference chamber, and the third reference chamber may be provided in a concentric arrangement on the microfluidic device.

The first reference chamber, the second reference chamber, and the third reference chamber may be provided at about equal intervals on the microfluidic device along a circumferential direction of the microfluidic device.

The third reference chamber, the first reference chamber, and the detection chamber may be provided in a concentric arrangement on the microfluidic device.

The at least one reference chamber may include only a single reference chamber, and the controller may detect the plurality of reference transmitted light intensities for the reference chamber and may estimate a value between the detected reference transmitted light intensities through nonlinear approximation.

The controller may detect the plurality of reference transmitted light intensities during a plurality of rotation periods of the microfluidic device.

The light absorbance measurement method and apparatus according to exemplary embodiments estimate a reference transmitted light intensity, corresponding to the time of measurement of a transmitted light intensity of the detection chamber, through nonlinear approximation and measures the light absorbance of the detection chamber using the estimated reference transmitted light intensity. Therefore, the light absorbance measurement method and apparatus reduces a light absorbance error caused by variation in the intensity of emission of the light source used for light absorbance detection and enables rapid light absorbance measurement. Especially, the light absorbance measurement method may significantly reduce a standby time for stabilization of the light source, thereby enabling rapid light absorbance measurement when a number of light sources are alternately used.

BRIEF DESCRIPTION OF THE DRAWINGS

The above and/or other aspects will become apparent and more readily appreciated from the following description of exemplary embodiments, taken in conjunction with the accompanying drawings of which.

DETAILED DESCRIPTION

Figure 1:
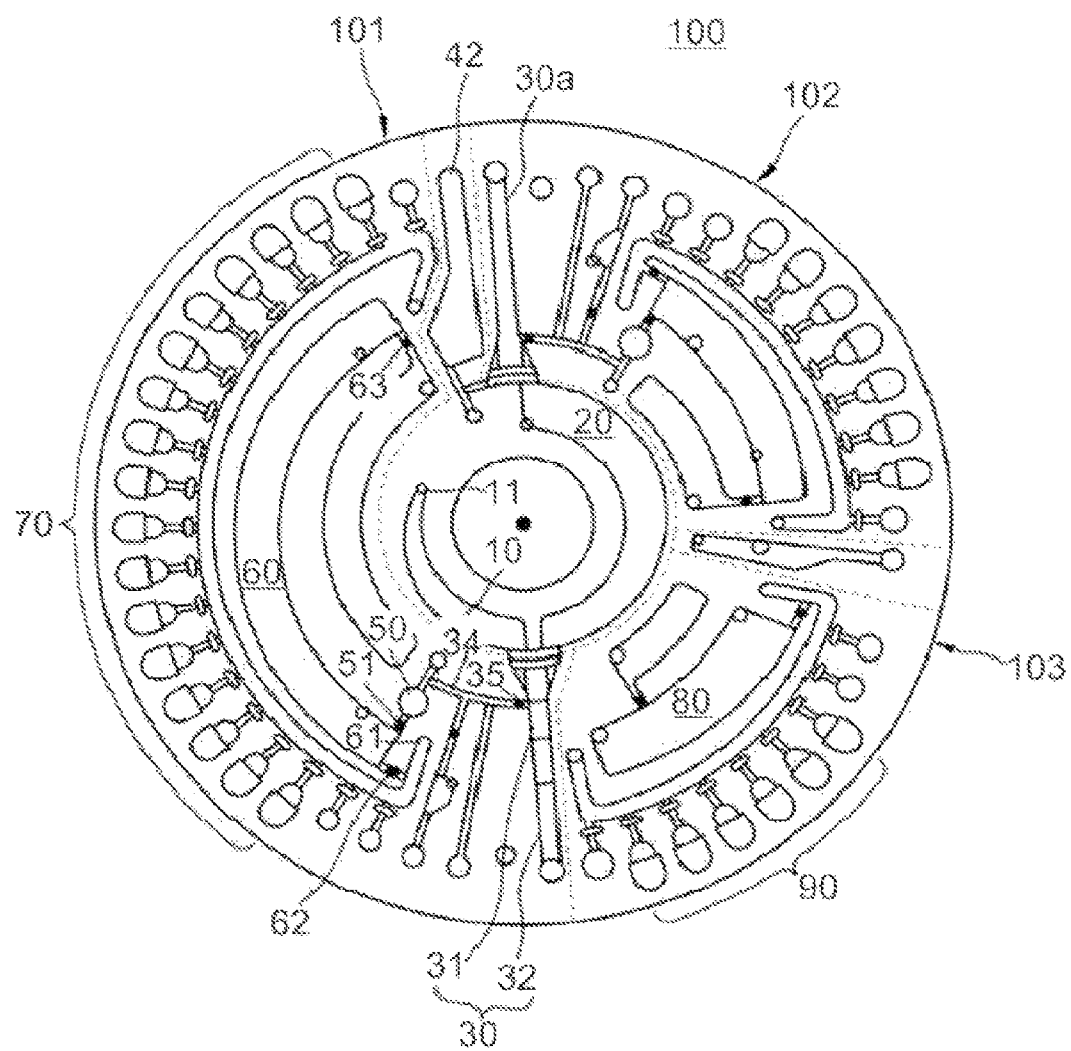
FIG. 1 illustrates a microfluidic device to which a light absorbance measurement method and apparatus may be applied, according to an embodiment.

Reference will now be made in detail to the exemplary embodiments, examples of which are illustrated in the accompanying drawings, wherein like reference numerals refer to like elements throughout.

Exemplary embodiments are described below with reference to FIGS. 1 to 9. First, FIG. 1 illustrates a microfluidic device to which a light absorbance measurement method and apparatus may be applied, according to an exemplary embodiment. As shown in FIG. 1, the microfluidic device 100 has a space that may accommodate fluid and microfluidic structures that provide flow paths through which fluid may flow. Centrifugal force due to rotation of the microfluidic device 100 causes fluid to be moved and mixed in the microfluidic structures.

The microfluidic device 100 may be made of plastic such as acryl or polydimethylsiloxane (PDMS) which is easily formed and the surface of which is biologically inert. However, the microfluidic device 100 is not necessarily made of plastic and may be made of any material which has chemical and biological stability, optical transparency, and mechanical workability. The microfluidic device 100 may include multi-layer plates. Incised structures for chambers, channels, or the like may be formed on opposing surfaces of the plates and the plates may then be joined to one another to provide fluid accommodation spaces and fluid passages. The plates may be joined to one another in a variety of ways, such as using an adhesive or a double-faced adhesive tape, ultrasonic fusion bonding, laser welding, or the like.

As shown in FIG. 1, the microfluidic device 100 includes a sample chamber 10. The sample chamber 10 accommodates a sample (for example, a biological sample such as blood). The sample chamber 10 may have an injection opening 11 through which a sample may be injected into the sample chamber 10. The microfluidic device 100 may include two or more sample chambers and two or more analysis units to receive samples from the sample chambers and to perform an analysis process on the samples. The microfluidic device 100 shown in FIG. 1 includes first analysis unit 101 and second analysis unit 102 that receive a sample from, for example, one sample chamber 10.

The first analysis unit 101 and second analysis unit 102 may be units to check blood test items that require different dilution ratios. For example, Albumin (ALB), Amylase (AMY), Urea Nitrogen (BUN), calcium (Ca++), Total Cholesterol (CHOL), Chloride (Cl—), Creatinine (CRE), Glucose (GLU), Gamma Glutamyl Transferase (GGT), High-Density Lipoprotein cholesterol (HDL), K+(K+Potassium), Lactate Dehydrogenase (LD), Sodium (Na+), Total Carbon dioxide (TCO2), Total Protein (TP), Triglyceride (TRIG), and Uric Acid (UA) are blood test items that require a dilution ratio of 1:100 of serum to diluent. In addition, alanine aminotransferase (ALT), Alkaline Phosphatase (ALP), aspartate aminotransferase (AST), Creatine Kinase (CK), Direct Bilirubin (D-BIL), and Total Bilirubin (T-BIL) are blood test items that require a dilution ratio of 1:20. The first analysis unit 101 may be a unit to check test items that require a dilution ratio of 1:100 and the second analysis unit 102 may be a unit to check test items that require a dilution ratio of 1:20. In another example, the first and second analysis units 101 and 102 may be units to check test items requiring the same dilution ratio. The following description is given only of a schematic configuration of the first analysis unit 101 since the configurations of the first and second analysis units 101 and 102 are substantially identical.

A sample distributer 30 receives blood from the sample chamber 10 and may have, for example, a volume requirement of a volume of blood required to measure the quantity of blood required for tests. The sample distributer 30 may serve as a centrifugal separator that separates blood into a supernatant and a sediment using the centrifugal force generated by rotation of the microfluidic device 100. For example, to accomplish this separation of blood, the sample distributer 30 may include a channel-shaped supernatant collector 31 which extends radially and outwardly and a sediment collector 32 which is located at an end of the supernatant collector 31 and which provides a space to collect a sediment having a high specific gravity.

The sample distributer 30 of the first analysis unit 101 is directly connected to the sample chamber 10 to receive a supernatant. A sample distributer 30a of the second analysis unit 102 is connected to the sample distributer 30 through a sample conveyance portion 20. Thus, the supernatant is provided from the sample chamber 10 to the sample distributer 30 to fill the sample distributer 30 and is then provided to the sample distributer 30a through the sample conveyance portion 20 to fill the sample distributer 30a. Supernatant remaining after filling the sample distributer 30a is accommodated in a surplus sample chamber 42.

The supernatant collected at an end of the supernatant collector 31 is then distributed to a next structure through a sample distribution channel 34. The sample distribution channel 34 may be provided with a valve 35 to control supernatant flow.

Any of various types of valves may be employed as the valve 35. The valve may be a capillary valve which is passively opened when a pressure greater than a certain level is applied, or a valve which receives power or energy from the outside through an activation signal and which is actively operated using the received power or energy. The valve 35 of this embodiment is a normally closed valve which closes the sample distribution channel 34 to prevent fluid flow until the valve absorbs electromagnetic energy.

The normally closed valve may include a valve material which is solid at room temperature. The valve material is present in a solid state in the channel to close the channel. The valve material melts at a high temperature to move into an inner space of the channel and is then coagulated again with the channel opened. For example, the energy emitted to the valve from the outside may be electromagnetic waves, and the energy source may be a laser light source that emits a laser beam, a Xenon lamp or a light emitting diode (LED) that emits visible light or infrared light. When the energy source is a laser light source, it may include at least one laser diode. A thermoplastic resin, a phase change material, or the like may be employed as the valve material. The phase change material may be wax, gel, or a thermoplastic resin. A number of microscopic exothermic particles which absorb electromagnetic energy to generate heat may be distributed in the valve material. The microscopic exothermic particles are uniformly spread in the valve material, and have properties such that their temperature is rapidly raised to generate heat, for example, when they are supplied with electron energy from the laser light. The microscopic exothermic particles may have a core containing metal components and a hydrophobic surface structure. The microscopic exothermic particles may be stored in a distributed manner in carrier oil. The carrier oil may also be hydrophobic so that microscopic exothermic particles having a hydrophobic surface structure are uniformly distributed.

The sample distribution channel 34 is connected to a supernatant measurement chamber 50 that accommodates a fixed quantity of supernatant. The supernatant measurement chamber 50 is connected to a dilution chamber 60 through a valve 51. A microfluidic valve of the same type as the valve 35 described above may be employed as the valve 51.

The dilution chamber 60 provides a diluted sample in which a supernatant and a diluent are mixed in a specific ratio. The dilution chamber 60 accommodates a quantity of diluent determined by taking into consideration the dilution ratio between the supernatant and the diluent required for the test. The supernatant measurement chamber 50 may be designed so as to have a volume that may accommodate a diluent in a quantity determined by taking into consideration the dilution ratio. As long as the valve 51 is kept closed, a sample which exceeds the volume of the supernatant measurement chamber 50 cannot flow into the supernatant measurement chamber 50. Accordingly, only a fixed quantity of diluent may be provided to the dilution chamber 60.

Detection chambers 70 are arranged outside the dilution chamber 60. The detection chambers 70 are connected to the dilution chamber 60 through a distribution channel 61. Distribution of the diluted sample through the distribution channel 61 may be controlled by a valve 62. A valve 63 serves to provide an air vent path so that the diluted sample can be easily distributed to the detection chambers 70. A microfluidic valve of the same type as the valve 35 described above may be employed as each of the valves 62 and 63. The detection chambers 70 accommodate reagents that cause different chemical reactions with the diluted sample.

The microfluidic device 100 may include a reference unit 103 that does not receive a sample from the sample chamber 10. The reference chamber 90 may be empty or may accommodate distilled water or a diluent. The distilled water or the diluent may be provided from a dilution chamber 80 to the reference chamber 90. The reference chamber 90 provides a reference light intensity used to detect light absorbance. Here, one or more reference chambers 90 may be provided.

Reagents may be accommodated in a liquid state or a freeze-dried state in the detection chambers 70. A cartridge (not shown) in which freeze-dried reagents are accommodated may be received in the detection chambers 70.

A diluted sample obtained by mixing the sample and the diluent is mixed with the reagents in the detection chambers 70. Each reagent reacts with a specific substance included in the diluted sample to exhibit a specific color and light absorbance of the mixture of the diluted sample and the reagent. A test subject is detected using the light absorbance detection method described above, thereby determining whether or not a specific component is present in the sample and/or the amount of the component in the sample.

Figure 2A:
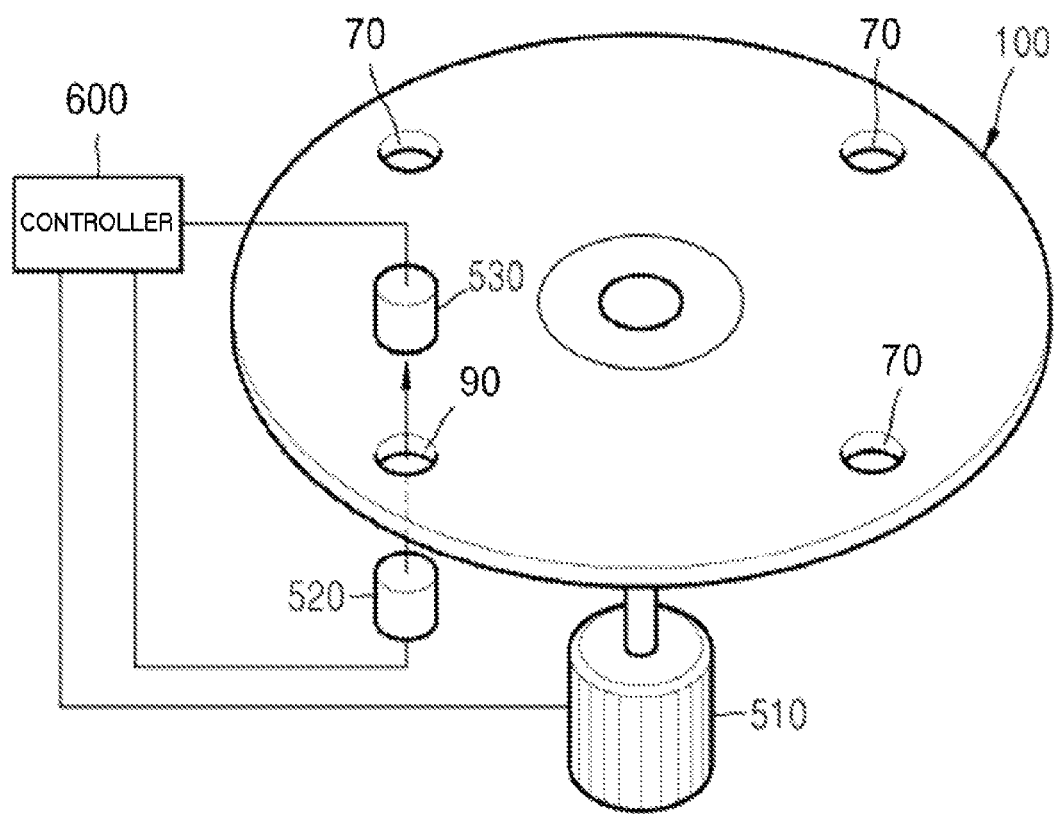
FIG. 2A illustrates a schematic configuration of an exemplary embodiment of a light absorbance measurement apparatus, according to an embodiment.

FIG. 2A illustrates a schematic configuration of an exemplary embodiment of a light absorbance measurement apparatus. As shown in FIG. 2A, the light absorbance measurement apparatus includes a microfluidic device 100, a rotation driver 510, a light source 520, an optical detector 530, and a controller 600.

The microfluidic device 100 is provided with detection chambers 70 that accommodate a test subject and a reference chamber 90 that provides a reference value for light absorbance detection. The microfluidic device 100 may be, for example, disc-shaped. The detection chambers 70 and the reference chamber 90 are arranged in a rotation direction of the microfluidic device 100, for example, in a circumferential direction of the microfluidic device 100 when the microfluidic device 100 is disc-shaped. The test subject is accommodated in the detection chambers 70. The reference chamber 90 provides a reference for light absorbance measurement and may be empty or filled with distilled water or the like.

The rotation driver 510 rotates the microfluidic device 100. The rotation driver 510 rotates the microfluidic device 100 to provide centrifugal force to separate a supernatant from the sample and to move the separated supernatant to a specific location in the microfluidic device 100 as needed. The rotation driver 510 also rotates the microfluidic device 100 to position each of the detection chambers 70 and the reference chamber 90 between the light source 520 and the optical detector 530. The rotation driver 510 may include a motor driver that may control angular position of the microfluidic device 100, although not illustrated. For example, the motor driver may use a stepper motor or may use a DC motor.

The light source 520 emits light of a specific wavelength to the detection chambers 70 and the reference chamber 90. The type of the light source 520 is not specifically limited. For example, a light emitting diode (LED) may be employed as the light source 520.

The optical detector 530 detects optical characteristics such as flourescence, emission, and/or light absorbance characteristics of a material to be detected. For example, the optical detector 530 may be a photo-sensor that generates a detection signal corresponding to the intensity of light that has been transmitted through the detection chamber 70 or the reference chamber 90.

The controller 600 controls operation timings of the rotation driver 510, the light source 520, and the optical detector 530. For example, the controller 600 detects a rotation phase of the rotation driver 510 and controls the light source 520 and the optical detector 530 to measure the intensity of light transmitted through the detection chamber 70 or the reference chamber 90 in synchronization with the detected rotation phase. For example, the microfluidic device 100 may be provided with a mark (not shown) to indicate a reference position. An angular distance between each detection chamber 70 and the reference chamber 90 is predetermined as a design specification of the microfluidic device 100. The controller 600 may control operations of the light source 520 and the optical detector 530 using the rotation speed of the microfluidic device 100, the mark, and the angular distance between the detection chamber 70 and the reference chamber 90 to allow the light source 520 and the optical detector 530 to perform light absorbance detection when the detection chamber 70 or the reference chamber 90 is positioned between them.

The controller 600 determines the intensity of light transmitted through the detection chamber 70 and the intensity of light transmitted through the reference chamber 90 using detection signals of the optical detector 530. The controller 600 then determines light absorbance of the detection chamber 70, specifically, light absorbance of the test subject accommodated in the detection chamber 70, using a ratio between the determined intensities of transmitted light. Although not illustrated, to accomplish this, the controller 600 may include, for example, a current-voltage converter that converts a detection signal which has a current signal form with a level proportional to the intensity of transmitted light into a voltage signal; an amplifier that amplifies the converted voltage signal; and an arithmetic unit that determines the intensity of transmitted light from the amplified voltage signal. The light absorbance is then calculated from the determined intensity of transmitted light.

The intensities of transmitted light of the detection chamber 70 and the reference chamber 90 cannot be measured simultaneously, but instead are measured at a time interval therebetween since they are measured using the same pair of the light source 520 and the optical detector 530. An error occurs in light absorbance detection if the intensity of emission of the light source 520 changes during the time interval. To reduce the light absorbance detection error caused by variation in the intensity of emission of the light source 520, the controller 600 of this embodiment approximates the intensity of transmitted light of the reference chamber 90 by a reference intensity of transmitted light corresponding to the time of detection of the intensity of transmitted light of the detection chamber 70 and calculates light absorbance using a ratio between the approximated reference transmitted light intensity and the transmitted light intensity of the detection chamber 70. To accomplish this calculation, the controller 600 of this exemplary embodiment estimates a value between at least two detected values of the intensity of transmitted light obtained through detection of at least one reference chamber using nonlinear approximation and applies the estimated value to calculation of the light absorbance of the detection chamber, thereby reducing a light absorbance error of the detection chamber.

Figure 2B:
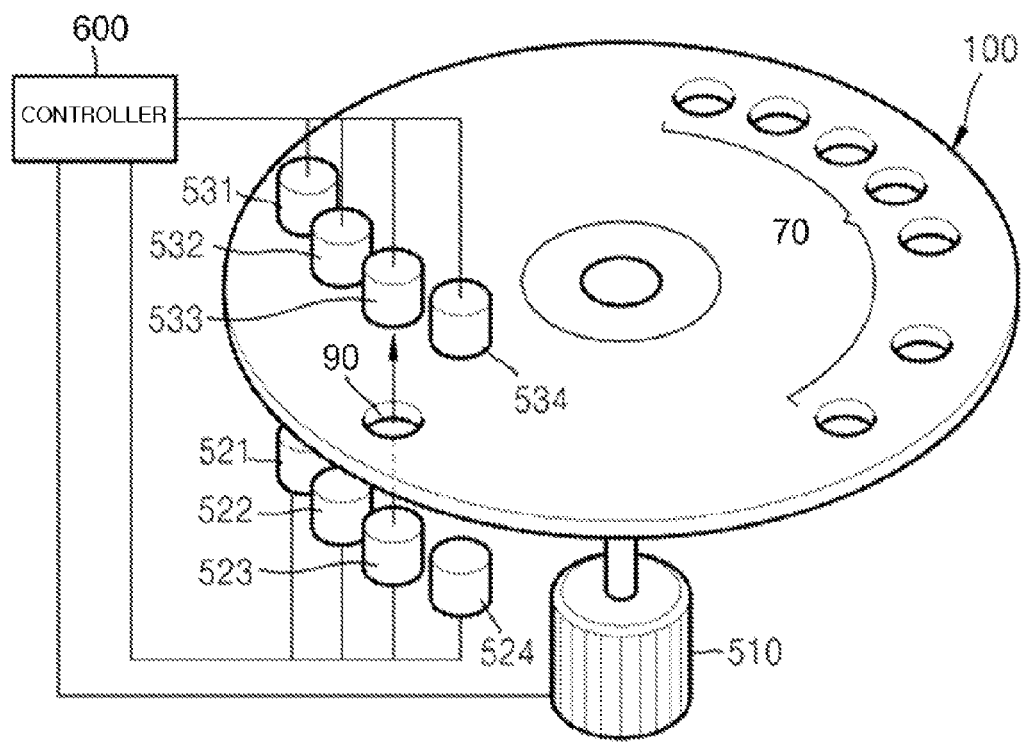
FIG. 2B schematically illustrates a light absorbance measurement apparatus according to another exemplary embodiment.

FIG. 2B schematically illustrates a light absorbance measurement apparatus according to another exemplary embodiment. As shown in FIG. 2B, the light absorbance measurement apparatus includes a plurality of light sources 521 to 524 and a plurality of light detectors 531 to 534 that are arranged in association with the plurality of light sources 521 to 524, respectively. The wavelength of light used to measure light absorbance may vary depending on a test subject that is to be detected by each detection chamber 70. To accomplish this, the light sources 521 to 524 emit light of different wavelengths. Although this embodiment is described with reference to an example wherein the light absorbance measurement apparatus includes four light sources and four corresponding optical detectors, the scope of the exemplary embodiment is not limited to this example. For example, the light absorbance measurement apparatus may include a plurality of light sources to emit light of wavelengths of approximately 340 nanometers (nm), 405 nm, 450 nm, 500 nm, 550 nm, 570 nm, 600 nm, 630 nm, 660 nm, and 700 nm to a plurality of corresponding optical detectors.

When light absorbance is being measured using one light source and one optical detector, for example, using the light source 521 and the optical detector 531 in the light absorbance measurement apparatus constructed as described above, the other light sources 522, 523, and 524 are turned off. This serves to prevent the occurrence of an error in light absorbance measurement due to stray light incident from the other light sources 522, 523, and 524.

The plurality of light sources 521 to 524 are arranged at specific intervals along the circumferential direction of the microfluidic device 100. The plurality of light detectors 531 to 534 are arranged in association with the plurality of light sources 521 to 524, respectively. For example, the controller 600 may perform a switching control operation to turn off the light source 521 and to turn on the light source 522 during a time interval in which the reference chamber 90 moves from a position at which it faces the light source 521 to a position at which it faces another light source 522. During this switching control operation, the microfluidic device 100 rotates immediately after the light absorbance measurement using the light source 521 and the optical detector 531 is finished. The light absorbance measurement method of this exemplary embodiment may perform light absorbance measurement while switching light sources very quickly since light absorbance measurement is possible even immediately after a light source is turned on. Although only one reference chamber 90 is illustrated in FIG. 2B, a plurality of reference chambers 90 may be provided as described above with reference to FIG. 1.

Light absorbance A may be defined as a ratio between light transmittance (Tref) of the reference chamber 90 and light transmittance (Tsamp) of the detection chamber 70. That is, the light absorbance A may be expressed as follows.

$$\text{Absorbance }(A) \equiv \log\left(\frac{T_{ref}}{T_{samp}}\right)$$

Light transmittance can be obtained using the reference transmitted light intensity of the reference chamber 90 and the detected transmitted light intensity of the detection chamber 70. Thus, first, the reference transmitted light intensity of the reference chamber 90 and the detected transmitted light intensity of the detection chamber 70 are measured to calculate light transmittance. Light absorbance is then calculated from the light transmittance. The light transmittance is calculated based on a ratio between the intensity of light emitted from the light source 520 to the reference or detection chamber 90 or 70 and the reference or detection transmitted light intensity of the reference or detection chamber 90 or 70. However, the reference transmitted light intensity of the reference chamber 90 and the detection transmitted light intensity of the detection chamber 70 cannot be measured simultaneously when only one pair of the light source 520 and the optical detector 530 is used. To accurately measure the reference transmitted light intensity of the reference chamber 90 and the detection transmitted light intensity of the detection chamber 70, the emission intensity of the light source 520 should be equal when the two transmitted light intensities are detected. If the intensities of emission of the light source 520 when the two transmitted light intensities are detected are different, the difference causes a light transmittance measurement error, making light absorbance detection results unreliable. Generally, the intensity of emission of the light source 520 varies depending on temperature and with time after the light source 520 is turned on. The intensity of emission of the light source 520 rapidly varies immediately after the light source 520 is turned on and is then stabilized at a constant level when a certain time has elapsed. Thus, to reduce the light absorbance measurement error, a stabilization time of tens of seconds to tens of minutes may be required depending on the characteristics of the light source 520. Even after the light source 520 is stabilized, environmental factors such as temperature change may cause variation in the intensity of emission of the light source 520, thereby causing a light absorbance error.

When the intensity of transmitted light of each of the reference chamber 90 and the detection chamber 70 is measured during one rotation period of the microfluidic device 100, the light absorbance error increases as the angular distance between the reference chamber 90 and the detection chamber 70 increases. The light absorbance measurement error may further increase as the time interval increases between when the reference transmitted light intensity of the reference chamber 90 is detected and when the detection transmitted light intensity of the detection chamber 70 is detected.

As a method to reduce a light absorbance measurement error caused by both the difference between the respective times of measurement of the transmitted light intensities of the reference chamber 90 and the detection chamber 70 and variation in the intensity of emission of the light source 520, the exemplary embodiment suggests a method in which the reference transmitted light intensity of the reference chamber 90 is nonlinearly approximated by a reference transmitted light intensity corresponding to the time of detection of the transmitted light intensity of the detection chamber 70. The light absorbance of the detection chamber 70 is measured using the nonlinearly approximated value of the reference transmitted light intensity of the reference chamber 90. This light absorbance measurement method significantly reduces the standby time until the light source 520 is stabilized while further increasing the accuracy of light absorbance.

This light absorbance measurement method may be extended. That is, a method to nonlinearly approximate the reference transmitted light intensity by detecting the light intensity using a single reference chamber a number of times over a number of rotation periods of the microfluidic device 100 or a method to nonlinearly approximate the reference transmitted light intensity by detecting the light intensity using a number of reference chambers in a single rotation period may be appropriately selected as needed to achieve an appropriate tradeoff between light absorbance detection time and light absorbance accuracy.

Figure 3:
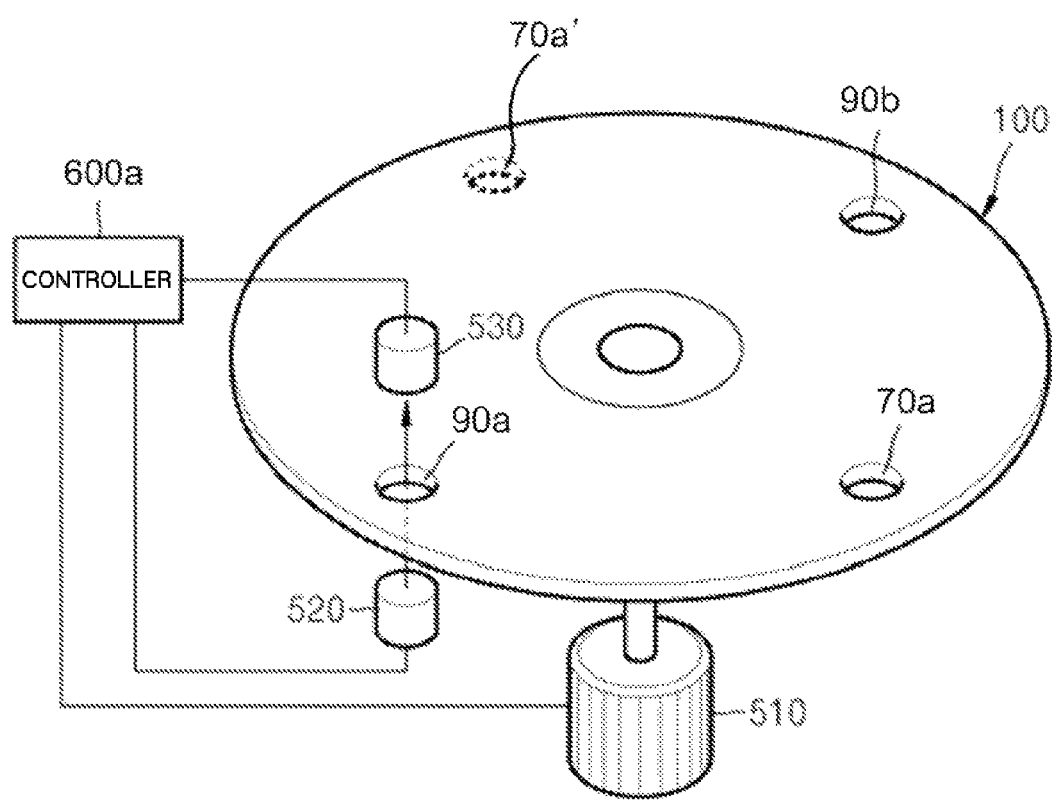
FIG. 3 illustrates a light absorbance measurement apparatus according to another exemplary embodiment.

FIG. 3 illustrates a light absorbance measurement apparatus according to another exemplary embodiment. In FIG. 3, the light absorbance measurement apparatus is briefly shown by partially modifying or omitting the light absorbance measurement apparatus of FIG. 1. As shown in FIG. 3, two reference chambers, i.e., first and second reference chambers 90a and 90b, are symmetrically provided on the microfluidic device 100. A detection chamber 70a is provided between the first and second reference chambers 90a and 90b. The positions of the first and second reference chambers 90a and 90b are not necessarily exactly symmetrical to each other and the detection chamber 70a may be provided at any position between the first and second reference chambers 90a and 90b. The first reference chamber 90a, the second reference chamber 90b, and the detection chamber 70a may be located in a concentric arrangement on the microfluidic device 100 such that each member is the same radial distance from the center of the microfluidic device 100. This makes it possible to detect the transmitted light intensities of the first reference chamber 90a, the second reference chamber 90b, and the detection chamber 70a on the rotating microfluidic device 100 without moving the light source 520 and the optical detector 530. A controller 600a calculates light absorbance of the detection chamber 70a through nonlinear approximation of a reference transmitted light intensity between the transmitted light intensities measured by the first reference chamber 90a and the second reference chamber 90b.

The transmitted light intensities of the first reference chamber 90a, the second reference chamber 90b, and the detection chamber 70a shown in FIG. 3 are detected in the following order. That is, the transmitted light intensities of the first reference chamber 90a and the second reference chamber 90b are sequentially detected in a specific rotation period of the microfluidic device 100 which rotates in a counterclockwise direction. Then, the transmitted light intensity of the first reference chamber 90a is again detected at an end time of the rotation period. The transmitted light intensity of the detection chamber 70a is detected before the transmitted light intensity of the first reference chamber 90a is again detected, but after the transmitted light intensity of the second reference chamber 90b is detected. A transmitted light intensity between the respective times of two detections of the transmitted light intensity of the first reference chamber 90a is estimated through nonlinear approximation of the three transmitted light intensities obtained in this manner, and the estimated transmitted light intensity is applied to calculation of the light absorbance of the detection chamber 70a. This allows more accurate calculation of the light absorbance than when transmitted light intensities respectively detected at the first and second reference chambers 90a and 90b are applied to light absorbance calculation of the detection chamber 70a.

In the embodiment of FIG. 3, the detection chamber 70a may be formed at a second position denoted by 70a', the second position being opposite the current position of the detection chamber 70a. In this case, the transmitted light intensity of the detection chamber 70a is detected at a time point indicated by an arrow 70a' in FIG. 4. As can be seen from the transmitted light intensity characteristics curve of FIG. 4, the respective times of detections of the reference transmitted light intensity and the detection transmitted light intensity may be changed depending on the positions of the first and second reference chambers 90a and 90b and the detection chamber 70a. Changing the time of detection of transmitted light intensity in this manner may be accomplished by providing a plurality of reference chambers and a plurality of detection chambers.

Figure 4:
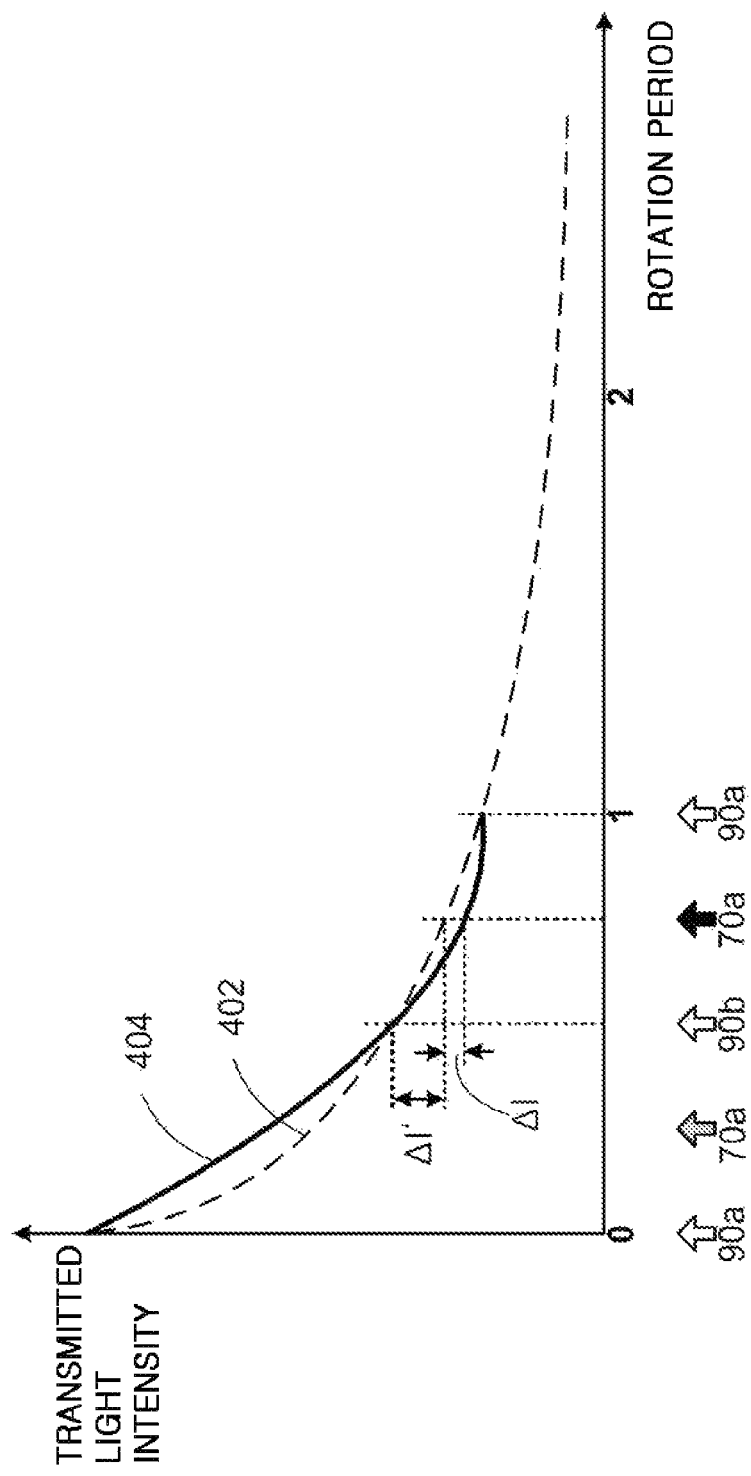
FIG. 4 illustrates results of transmitted light intensity detection and nonlinear approximation for light absorbance measurement, according to the exemplary embodiment of FIG. 3.

FIG. 4 illustrates results of transmitted light intensity detection and nonlinear approximation for light absorbance measurement according to the embodiment of FIG. 3. In FIG. 4, the detection times of the reference transmitted light intensities of the first reference chamber 90a and the second reference chamber 90b are shown by white arrows and the detection time of the detection transmitted light intensity of the detection chamber 70a is shown by a black arrow. In FIG. 4, a dashed curve 402 represents an actual transmitted light intensity change curve obtained through actual transmitted light intensity detection and a solid curve 404 represents an approximation curve obtained through nonlinear approximation.

As can be seen from FIG. 4, a difference $\Delta 1'$ between the transmitted light intensity of the detection chamber 70a and the transmitted light intensity of the second reference chamber 90b and a difference $\Delta 1$ between the transmitted light intensity of the detection chamber 70a and a transmitted light intensity approximated at the same time as when the transmitted light intensity of the detection chamber 70a is detected satisfy a relationship of $\Delta 1 < \Delta 1'$. Thus, a light absorbance measurement error is significantly reduced when the light absorbance of the detection chamber 70a is calculated using the approximated transmitted light intensity. In addition, since the light absorbance measurement error is greatly reduced even when light absorbance measurement is performed before the light source is sufficiently stabilized, the standby time until the light source is stabilized is significantly reduced, thereby allowing rapid light absorbance measurement.

Figure 5:
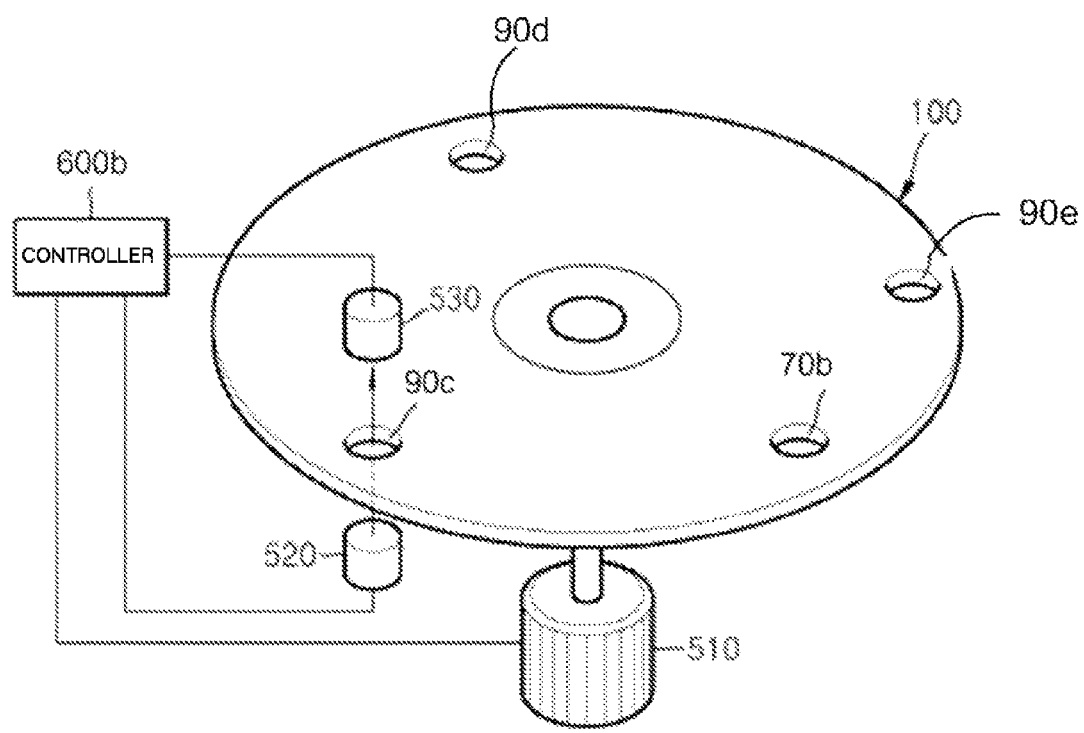
FIG. 5 illustrates a light absorbance measurement apparatus according to another exemplary embodiment.

FIG. 5 illustrates a light absorbance measurement apparatus according to another exemplary embodiment. In FIG. 5, the light absorbance measurement apparatus is briefly shown by partially modifying or omitting the light absorbance measurement apparatus of FIG. 1. As shown in FIG. 5, three reference chambers, i.e., first chamber 90c, second chamber 90d and third reference chamber 90e, are provided at equal intervals of, for example, 120° along the circumferential direction of the microfluidic device 100. A detection chamber 70b is provided between the first reference chamber 90c and the third reference chamber 90e. The first reference chamber 90c, second reference chamber 90d, and third reference chamber 90e may be provided at unequal intervals, as needed, and the detection chamber 70b may be provided at any position between the first reference chamber 90c and the second reference chamber 90d or between the second reference chamber 90d and the third reference chamber 90e. The first reference chamber 90c, the second reference chamber 90d, the third reference chamber 90e, and the detection chamber 70b may be located in a concentric arrangement on the microfluidic device 100. This configuration makes it possible to detect the transmitted light intensities of the first reference chamber 90c, the second reference chamber 90d, the third reference chamber 90e, and the detection chamber 70b on the rotating microfluidic device 100 without moving the light source 520 and the optical detector 530. A controller 600b calculates light absorbance of the detection chamber 70b through nonlinear approximation of a reference transmitted light intensity between the transmitted light intensities measured by the first reference chamber 90c, the second reference chamber 90d and the third reference chamber 90e.

Similar to the exemplary embodiment of FIGS. 3 and 4, the detection chamber 70b may be formed between the first reference chamber 90c and the second reference chamber 90d or between the second reference chamber 90d and the third reference chamber 90e. In this case, the transmitted light intensity of the detection chamber 70b may be detected at a time different from that indicated by an arrow 70b in FIG. 6. As can be seen from the transmitted light intensity characteristics curve of FIG. 6, the respective times of detections of the reference transmitted light intensity and the detection transmitted light intensity may be changed depending on the positions of the first reference chamber 90c, second reference chamber 90d, and third reference chamber 90e and the detection chamber 70b. Changing the time of detection of transmitted light intensity in this manner may be accomplished by providing a plurality of reference chambers and a plurality of detection chambers.

The transmitted light intensities of the first reference chamber 90c, the second reference chamber 90d, the third reference chamber 90e, and the detection chamber 70b shown in FIG. 5 are detected in the following order. That is, the transmitted light intensities of the first reference chamber 90c, the second reference chamber 90d, and the third reference chamber 90e are sequentially detected in a specific rotation period of the microfluidic device 100 which rotates in a counter-clockwise direction. The transmitted light intensity of the first reference chamber 90c is then again detected at an end time of the rotation period. The transmitted light intensity of the detection chamber 70b is detected before the transmitted light intensity of the first reference chamber 90c is again detected, but after the transmitted light intensity of the third reference chamber 90e is detected. A transmitted light intensity between the respective times of two detections of the transmitted light intensity of the first reference chamber 90c is estimated through nonlinear approximation of the four transmitted light intensities obtained in this manner, and the estimated transmitted light intensity is applied to calculation of the light absorbance of the detection chamber 70b. This allows more accurate calculation of the light absorbance than when transmitted light intensities respectively detected at the first reference chamber 90c, second reference chamber 90d, and third reference chamber 90e are applied to light absorbance calculation of the detection chamber 70b.

Figure 6:
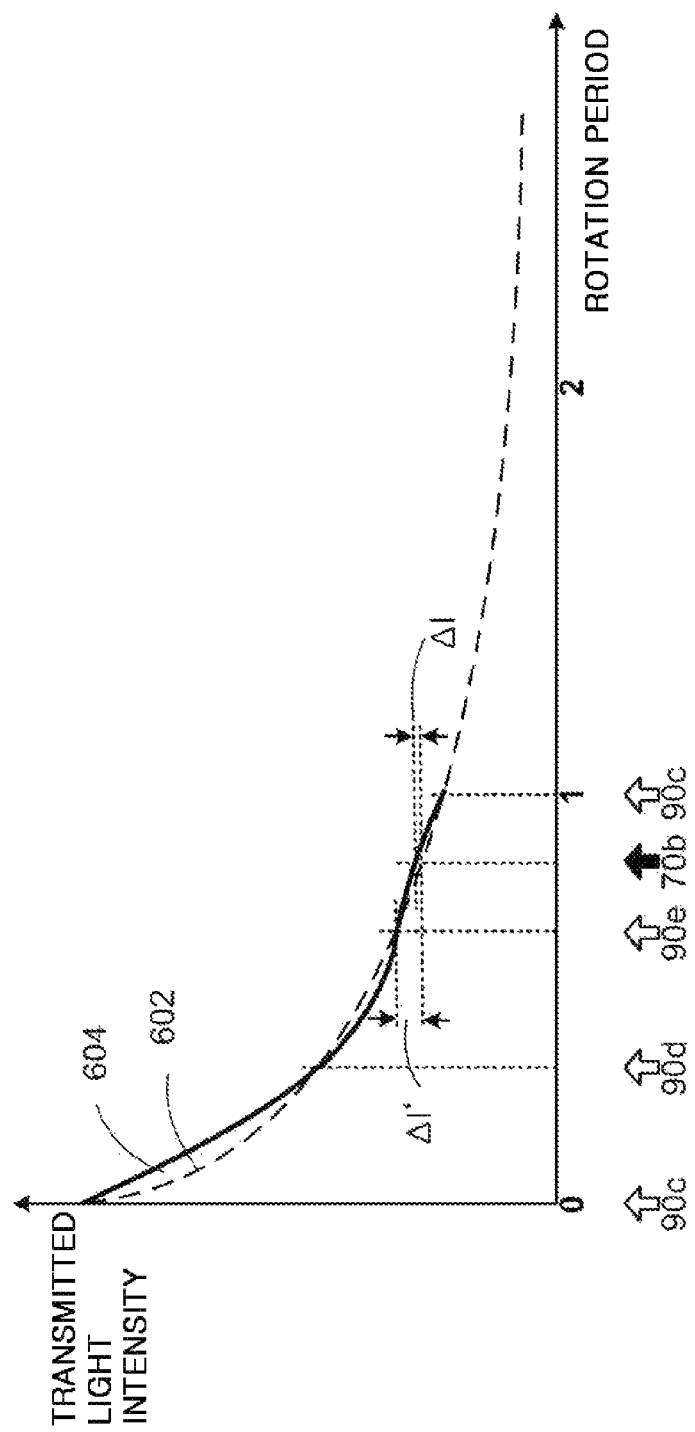
FIG. 6 illustrates results of transmitted light intensity detection and nonlinear approximation for light absorbance measurement, according to the exemplary embodiment of FIG. 5.

FIG. 6 illustrates results of transmitted light intensity detection and nonlinear approximation for light absorbance measurement according to the embodiment of FIG. 5. In FIG. 6, the detection times of the reference transmitted light intensities of the first reference chamber 90c, second reference chamber 90d, and third reference chamber 90e are shown by white arrows and the detection time of the transmitted light intensity of the detection chamber 70b is shown by a black arrow. In FIG. 6, a dashed curve 602 represents an actual transmitted light intensity change curve obtained through actual transmitted light intensity detection and a solid curve 604 represents an approximation curve obtained through nonlinear approximation.

As can be seen from FIG. 6, a difference $\Delta 1'$ between the transmitted light intensity of the detection chamber 70b and the transmitted light intensity of the third reference chamber 90e and a difference $\Delta 1$ between the transmitted light intensity of the detection chamber 70b and a transmitted light intensity approximated at the same time as when the transmitted light intensity of the detection chamber 70b is detected satisfy a relation of $\Delta 1 < \Delta 1'$. Thus, a light absorbance measurement error is significantly reduced when the light absorbance of the detection chamber 70b is calculated using the approximated transmitted light intensity. In addition, since the light absorbance measurement error is greatly reduced even when light absorbance measurement is performed before the light source is sufficiently stabilized, the standby time until the light source is stabilized is significantly reduced, thereby allowing rapid light absorbance measurement.

Although the exemplary embodiment of FIGS. 5 and 6 has a greater number of detection chambers and a greater number of detections than the exemplary embodiment of FIGS. 3 and 4, the exemplary embodiment of FIGS. 5 and 6, which performs nonlinear approximation using four detected transmitted light intensity values, has a lower light absorbance measurement error than the exemplary embodiment of FIGS. 3 and 4, which performs nonlinear approximation using three detected transmitted light intensity values as described above. This lower light absorbance error occurs since the approximation of the exemplary embodiment of FIGS. 5 and 6 may be closer to the actual value than the exemplary embodiment of FIGS. 3 and 4. As a result, the embodiment of FIGS. 5 and 6 may provide more accurate light absorbance detection results even though the number of detection chambers and the number of detections are increased, thereby significantly increasing reliability of the light absorbance detection results.

Figure 7:
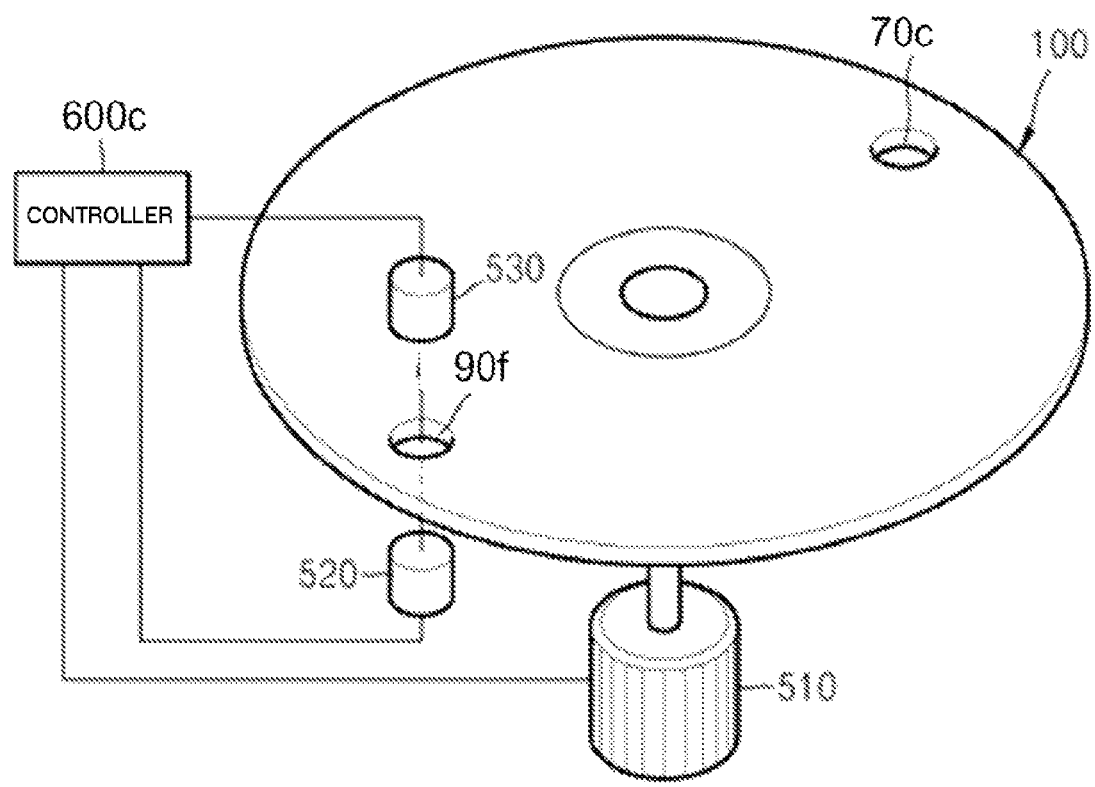
FIG. 7 illustrates a light absorbance measurement apparatus according to another exemplary embodiment.

FIG. 7 illustrates a light absorbance measurement apparatus according to another exemplary embodiment. In FIG. 7, the light absorbance measurement apparatus is briefly shown by partially modifying or omitting the light absorbance measurement apparatus of FIG. 1. As shown in FIG. 7, a single reference chamber 90f is provided on a microfluidic device 100 and a detection chamber 70c is provided at a position opposite the reference chamber 90f. The reference chamber 90f and the detection chamber 70c are not necessarily located opposite each other. The reference chamber 90f and the detection chamber 70c may be located in a concentric arrangement on the microfluidic device 100. This configuration makes it possible to detect the transmitted light intensities of the reference chamber 90f and the detection chamber 70c on the rotating microfluidic device 100 without moving the light source 520 and the optical detector 530. A controller 600c calculates light absorbance of the detection chamber 70c through nonlinear approximation using transmitted light intensities that the reference chamber 90f has measured respectively in a plurality of consecutive rotation periods.

As shown in FIG. 7, the transmitted light intensity of the reference chamber 90f is detected during every rotation period of the microfluidic device 100, which rotates in a counterclockwise direction. The transmitted light intensity of the detection chamber 70c is detected immediately before the last detection of the transmitted light intensity of the reference chamber 90f. The transmitted light intensity of the detection chamber 70c may be detected at a different time as needed. The number of detections of the transmitted light intensity of the reference chamber 90f may be increased when more accurate light absorbance detection is required. On the other hand, the number of detections of the transmitted light intensity of the reference chamber 90f is decreased when highly accurate light absorbance detection is not required. A transmitted light intensity is estimated through nonlinear approximation using a plurality of transmitted light intensities obtained in this manner and the estimated transmitted light intensity is applied to calculate of the light absorbance of the detection chamber 70c. This allows more accurate calculation of the light absorbance than when a transmitted light intensity detected at the reference chamber 90f is applied to light absorbance calculation of the detection chamber 70c.

Figure 8:
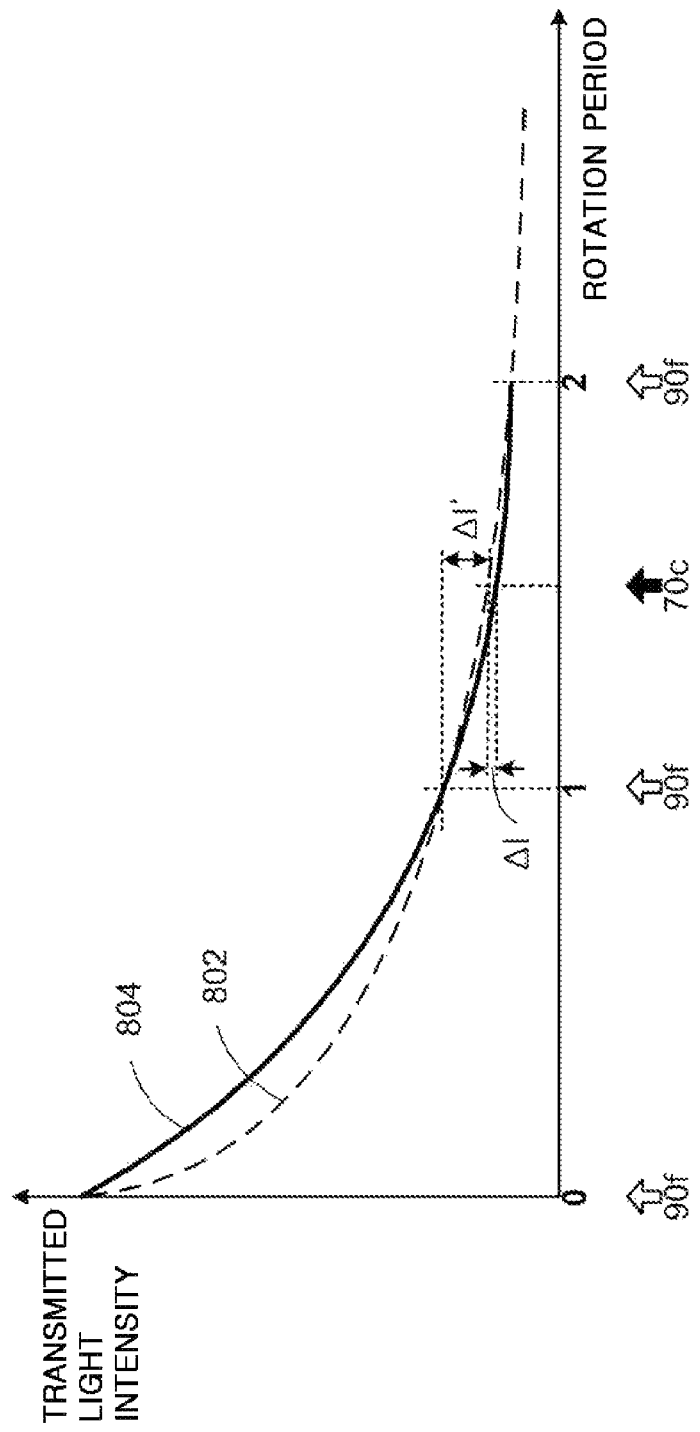
FIG. 8 illustrates results of transmitted light intensity detection and nonlinear approximation for light absorbance measurement, according to the exemplary embodiment of FIG. 7.

Similar to the exemplary embodiment illustrated in FIGS. 3 and 4 and the exemplary embodiment illustrated in FIGS. 5 and 6, the time of detection of the transmitted light intensity of the detection chamber 70c may be different from that indicated by an arrow 70c shown in FIG. 8 depending on the position of the detection chamber 70c. As can be seen from the transmitted light intensity characteristics curve of FIG. 8, the respective times of detections of the reference transmitted light intensity and the detection transmitted light intensity may be changed depending on the positions of the reference chamber 90f and the detection chamber 70c. Changing the time of detection of transmitted light intensity in this manner may be accomplished by providing a plurality of reference chambers and a plurality of detection chambers.

FIG. 8 illustrates results of transmitted light intensity detection and nonlinear approximation for light absorbance measurement according to the exemplary embodiment of FIG. 7. Specifically, FIG. 8 illustrates the case where the transmitted light intensity of the reference chamber 90f is detected over three rotation periods of the microfluidic device 100. In FIG. 8, the respective times of three detections of the reference transmitted light intensity of the reference chamber 90f are shown by white arrows and the detection time of the transmitted light intensity of the detection chamber 70c is shown by a black arrow. In FIG. 8, a dashed curve 802 represents an actual transmitted light intensity change curve obtained through actual transmitted light intensity detection and a solid curve 804 represents an approximation curve obtained through nonlinear approximation.

As can be seen from FIG. 8, a difference $\Delta 1'$ between the transmitted light intensity of the detection chamber 70c and the transmitted light intensity of the reference chamber 90e and a difference $\Delta 1$ between the transmitted light intensity of the detection chamber 70c and a transmitted light intensity approximated at the same time as when the transmitted light intensity of the detection chamber 70c is detected satisfy a relation of $\Delta 1 < \Delta 1'$. Thus, a light absorbance measurement error is significantly reduced when the light absorbance of the detection chamber 70c is calculated using the approximated transmitted light intensity. In addition, since the light absorbance measurement error is greatly reduced even when light absorbance measurement is performed before the light source is sufficiently stabilized, the standby time until the light source is stabilized is significantly reduced, thereby allowing rapid light absorbance measurement.

Although the exemplary embodiment of FIGS. 7 and 8 is similar to the exemplary embodiment of FIGS. 3 and 4 in that nonlinear approximation is performed using three detected transmitted light intensity values as described above, the exemplary embodiment of FIGS. 7 and 8 simplifies the configuration of the light absorbance measurement apparatus and reduces manufacturing costs since only one reference chamber is used.

Figure 9:
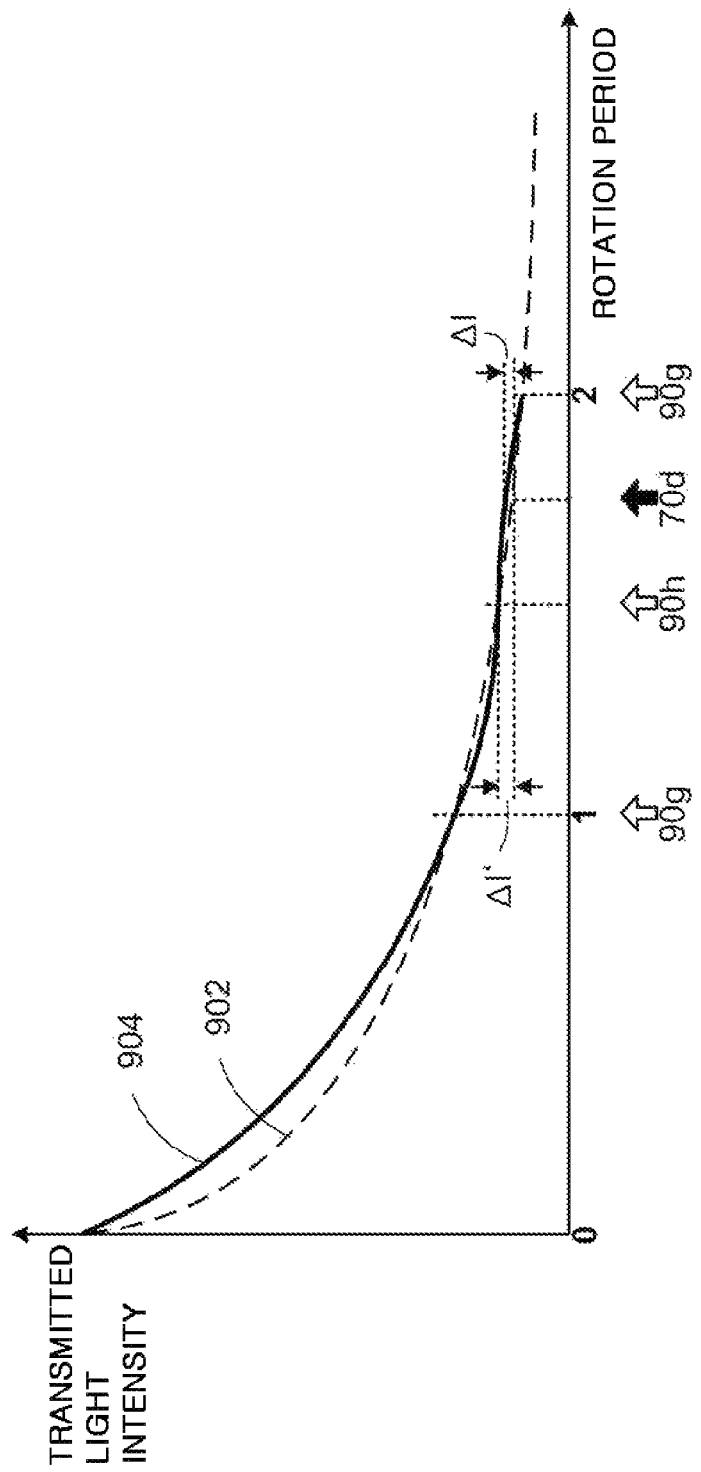
FIG. 9 illustrates results of transmitted light intensity detection and nonlinear approximation for light absorbance measurement, according to another exemplary embodiment.

FIG. 9 illustrates results of transmitted light intensity detection and nonlinear approximation for light absorbance measurement according to another exemplary embodiment. Specifically, FIG. 9 illustrates where the transmitted light intensity of the reference chamber 90f is detected in a second rotation period of the microfluidic device 100 after the light source 520 is turned on. In FIG. 9, the respective times of detections of the reference transmitted light intensity are shown by white arrows 90g and 90h and the detection time of the detection transmitted light intensity is shown by a black arrow 70d. In FIG. 9, a dashed curve 902 represents an actual transmitted light intensity change curve obtained through actual transmitted light intensity detection and a solid curve 904 represents an approximation curve obtained through nonlinear approximation.

As shown in FIG. 9, if the reference transmitted light intensity and the detection transmitted light intensity are detected in the second rotation period of the microfluidic device 100 and the light absorbance is measured through approximation using the detected transmitted light intensities, more accurate light absorbance measurement is achieved since the difference between an actual transmitted light intensity 902 and the approximated transmitted light intensity 904 is considerably reduced compared to the first period. Of course, although the time required for light absorbance detection increases as the number of rotations of the microfluidic device 100 increases, the method of FIG. 9 is a good way to increase light absorbance accuracy. Although the exemplary embodiment illustrated in FIGS. 3 and 4, the exemplary embodiment illustrated in FIGS. 5 and 6, and the exemplary embodiment illustrated in FIGS. 7 and 8 have been described above with reference to an example wherein transmitted light intensities are detected in the first rotation period of the microfluidic device 100 after the light source 520 is turned on, the reference transmitted light intensity and the detection transmitted light intensity may also be detected in one of the rotation periods (especially, a later one) other than the first rotation period to increase light absorbance measurement accuracy in the exemplary embodiment of FIGS. 3 and 4, the exemplary embodiment of FIGS. 5 and 6, and the exemplary embodiment of FIGS. 7 and 8, similar to the exemplary embodiment of FIG. 9.

As is apparent from the above description, the light absorbance measurement method and apparatus according to the exemplary embodiments estimate a reference transmitted light intensity, corresponding to the time of measurement of a transmitted light intensity of the detection chamber, through nonlinear approximation. The light absorbance of the detection chamber is then measured using the estimated reference transmitted light intensity. Therefore, the light absorbance measurement method and apparatus reduces a light absorbance measurement error caused by variation in the intensity of emission of the light source used for light absorbance detection and enables more rapid light absorbance measurement. Especially, the light absorbance measurement method significantly reduces a standby time for stabilization of the light source, thereby enabling more rapid light absorbance measurement when a number of light sources are alternately used.

Although the above exemplary embodiments have been described with reference to the microfluidic device 100 for blood biochemistry tests as an example, applications of the light absorbance measurement method and apparatus according to the exemplary embodiments are not limited to blood biochemistry tests. Those skilled in the art will appreciate that the light absorbance measurement method and apparatus according to the exemplary embodiments can be applied to any test subject that may be tested by light absorbance measurement.

Although a few exemplary embodiments have been shown and described, it would be appreciated by those skilled in the art that changes may be made in these exemplary embodiments without departing from the principles and spirit of the inventive concept, the scope of which is defined in the claims and their equivalents.

What is claimed is:

1. A method to measure light absorbance of at least one detection chamber of a microfluidic device which comprises at least one reference chamber and the at least one detection chamber accommodating a test subject, the method comprising:
   detecting a plurality of reference transmitted light intensities for the at least one reference chamber;
   estimating a value between the plurality of detected reference transmitted light intensities through nonlinear approximation; and
   applying the estimated value to determine light absorbance of the at least one detection chamber.

2. The method according to claim 1, wherein the light absorbance is determined as a ratio between a reference transmitted light intensity of the reference chamber and a detected transmitted light intensity of the at least one detection chamber.

3. The method according to claim 1, wherein a plurality of light sources which emit light of different wavelengths and a plurality of optical detectors corresponding to the plurality of light sources are provided at positions corresponding to positions of the at least one reference chamber and the at least one detection chamber,
   the method further comprising turning one of the plurality of light sources on and the other light sources off when performing transmitted light intensity detection.

4. The method according to claim 3, wherein the at least one reference chamber includes a first reference chamber and a second reference chamber, and
   the detecting the plurality of reference transmitted light intensities comprises detecting the plurality of reference transmitted light intensities in an order such that a reference transmitted light intensity of the first reference chamber is detected, a reference transmitted light intensity of the second reference chamber is detected, and a reference transmitted light intensity of the first reference chamber is again detected.

5. The method according to claim 4, wherein the plurality of reference transmitted light intensities is detected during one rotation period of the microfluidic device after one of the plurality of light sources is turned on.

6. The method according to claim 5, wherein the plurality of reference transmitted light intensities is detected during a first rotation period of the microfluidic device after one of the plurality of light sources is turned on.

7. The method according to claim 5, wherein the plurality of reference transmitted light intensities is detected during one rotation period, other than a first rotation period, of the microfluidic device after one of the plurality of light sources is turned on.

8. The method according to claim 5, wherein a transmitted light intensity of the detection chamber is detected during the same rotation period as the rotation period of the microfluidic device during which the plurality of reference transmitted light intensities is detected after one of the plurality of light sources is turned on.

9. The method according to claim 3, wherein the at least one reference chamber includes a first reference chamber, a second reference chamber, and a third reference chamber, and
   the detecting the plurality of reference transmitted light intensities comprises detecting the plurality of reference transmitted light intensities in an order such that a reference transmitted light intensity of the first reference chamber is detected, a reference transmitted light intensity of the second reference chamber is detected, a reference transmitted light intensity of the third reference chamber is detected, a reference transmitted light intensity of the first reference chamber is again detected.

10. The method according to claim 9, wherein the plurality of reference transmitted light intensities is detected during one rotation period of the microfluidic device after one of the plurality of light sources is turned on.

11. The method according to claim 10, wherein the plurality of reference transmitted light intensities is detected during a first rotation period of the microfluidic device after one of the plurality of light sources is turned on.

12. The method according to claim 10, wherein the plurality of reference transmitted light intensities is detected during one rotation period, other than a first rotation period, of the microfluidic device after one of the plurality of light sources is turned on.

13. The method according to claim 10, wherein a transmitted light intensity of the detection chamber is detected during the same rotation period as the rotation period of the microfluidic device during which the plurality of reference transmitted light intensities is detected after one of the plurality of light sources is turned on.

14. The method according to claim 3, wherein the at least one reference chamber includes only a single reference chamber.

15. The method according to claim 14, wherein the plurality of reference transmitted light intensities is detected during a plurality of rotation periods of the microfluidic device.

16. The method according to claim 15, wherein the plurality of reference transmitted light intensities is detected during a plurality of consecutive rotation periods of the microfluidic device including a first rotation period of the microfluidic device after one of the plurality of light sources is turned on.

17. The method according to claim 15, wherein the plurality of reference transmitted light intensities is detected during a plurality of consecutive rotation periods, other than a first rotation period, of the microfluidic device after one of the plurality of light sources is turned on.

18. The method according to claim 15, wherein a transmitted light intensity of the detection chamber is detected during the same rotation periods as the plurality of rotation periods of the microfluidic device during which the plurality of reference transmitted light intensities is detected after one of the plurality of light sources is turned on.

* * * * *